(12) United States Patent
Mandre et al.

(10) Patent No.: US 9,687,298 B2
(45) Date of Patent: Jun. 27, 2017

(54) LIGHT EMITTING DEVICE

(75) Inventors: Shyam Kishan Mandre, Hofheim (DE); Frank Beerwerth, Kaltenholzhausen (DE); Dimitri Bogatirsky, Eschborn (DE); Christian Neyer, Eschborn (DE)

(73) Assignee: Braun GmbH, Kronberg (DE)

( * ) Notice: Subject to any disclaimer, the term of this patent is extended or adjusted under 35 U.S.C. 154(b) by 0 days.

(21) Appl. No.: 13/614,518

(22) Filed: Sep. 13, 2012

(65) Prior Publication Data

US 2013/0066306 A1 Mar. 14, 2013

(30) Foreign Application Priority Data

Sep. 14, 2011 (EP) .................................... 11007458

(51) Int. Cl.
| | | |
|---|---|---|
| *A61N 5/06* | (2006.01) |
| *A61B 18/18* | (2006.01) |
| *A61B 18/20* | (2006.01) |
| *G01N 21/552* | (2014.01) |
| *G01N 33/543* | (2006.01) |
| *G01N 33/50* | (2006.01) |

(Continued)

(52) U.S. Cl.
CPC .. *A61B 18/203* (2013.01); *A61B 2018/00476* (2013.01); *A61B 2090/065* (2016.02); *G01N 21/552* (2013.01); *G01N 33/5005* (2013.01); *G01N 33/543* (2013.01)

(58) Field of Classification Search
CPC . G01N 21/552; G01N 33/543; G01N 33/5005
USPC ................................................ 606/9; 607/88
See application file for complete search history.

(56) References Cited

U.S. PATENT DOCUMENTS

| 4,254,333 A | 3/1981 | Bergstroem |
| 6,273,884 B1 | 8/2001 | Altshuler et al. |

(Continued)

FOREIGN PATENT DOCUMENTS

| DE | 19856008 A1 | 6/2000 |
| DE | 202005010570 U1 | 9/2005 |

(Continued)

OTHER PUBLICATIONS

European Search Report for EP 11 00 7458 dated Feb. 16, 2012.
International Search Report for PCT/IB2012/054830, dated Jan. 22, 2013.

*Primary Examiner* — Lynsey Crandall
*Assistant Examiner* — Sebastian X Lukjan
(74) *Attorney, Agent, or Firm* — Ronald T. Sia; Kevin C. Johnson; Steven W. Miller (57) ABSTRACT

A light emitting device for use as a hair removal device is provided. The light emitting device has at least one radiation source for electromagnetic radiation providing at least one operating beam during operation of the device, a housing being intransparent for the operating beam having an output opening, at least one radiation source for electromagnetic radiation providing at least one sensing beam during operation of the device, at least one detector for detecting the sensing beam, at least one sensing window having a contact boundary surface, and a controller communicating with the radiation source providing the operating beam and with a detector and being operable to influence operation of the radiation source providing the operating beam responsive to the sensing beam detected at the detector.

13 Claims, 10 Drawing Sheets

(51) Int. Cl.
  *A61B 18/00* (2006.01)
  *A61B 90/00* (2016.01)

(56) References Cited

U.S. PATENT DOCUMENTS

| | | | |
|---|---|---|---|
| 6,507,015 | B1 | 1/2003 | Maeno et al. |
| 6,641,578 | B2 | 11/2003 | Mukai |
| 6,758,845 | B1 | 7/2004 | Weckwerth et al. |
| 7,184,614 | B2 | 2/2007 | Slatkine |
| 7,250,045 | B2 | 7/2007 | Island et al. |
| 7,280,714 | B2 | 10/2007 | Reime et al. |
| 7,452,356 | B2 | 11/2008 | Grove et al. |
| 2004/0176825 | A1 | 9/2004 | Vaynberg et al. |
| 2006/0253176 | A1* | 11/2006 | Caruso et al. ............... 607/88 |
| 2007/0049910 | A1 | 3/2007 | Altshuler et al. |
| 2007/0060819 | A1* | 3/2007 | Altshuler et al. ........... 600/475 |
| 2008/0004611 | A1* | 1/2008 | Houbolt et al. ............... 606/9 |
| 2009/0287195 | A1* | 11/2009 | Altshuler et al. ............. 606/9 |

FOREIGN PATENT DOCUMENTS

| | | |
|---|---|---|
| DE | 102005021008 A1 | 12/2005 |
| WO | WO 86/05338 | 9/1986 |
| WO | WO 2006/038168 | 4/2006 |

\* cited by examiner

LIGHT EMITTING DEVICE

FIELD OF THE INVENTION

The present invention relates to the field of light emitting devices and further to the field of electrical household appliances, e.g. electromagnetic hair removal devices comprising a light emitting device.

BACKGROUND OF THE INVENTION

Laser hair removal or laser epilation technology is commonly used to remove hair from a person's skin or even to prevent growth of new hairs. The electromagnetic absorption of hair, in particular of hair roots in certain wavelength areas of electromagnetic radiation is larger than absorption by the surrounding skin. Accordingly when treating skin with light in a selected wavelength range the hair roots may be selectively heated up to temperatures above 60° C. leading to a loss of the hair roots' capability of producing new hair. Thus treatment by light may allow to manage hair growth on human skin.

Due to the necessity of high power light sources laser hair removal has been restricted to use in dedicated beauty salons and clinics over a long time.

However, there is a need for electromagnetic hair removal devices as electrical household appliances to be used by laymen at home. As electrical household appliances or personal care devices should be handheld devices, electromagnetic hair removal devices require a strict consideration of any safety issues.

Electrical household appliances containing high power light sources should avoid any intense light escaping from its housing in an uncontrolled manner.

Accordingly it is an object of this invention to provide a light emitting device enabling emission of laser radiation from a housing only under conditions reducing hazard for a consumer's eyes.

SUMMARY OF THE INVENTION

According to a first aspect of the invention there is provided a light emitting device comprising at least one radiation source for electromagnetic radiation providing at least one operating beam during operation of the device, a housing being intransparent for the operating beam having an output opening, wherein the radiation source providing the operating beam is located in the housing, and wherein the radiation source providing the operating beam and the output opening are arranged such that during operation of the device the operating beam may exit the housing through the output opening, at least one radiation source for electromagnetic radiation providing at least one sensing beam during operation of the device, at least one detector for detecting the sensing beam, at least one sensing window having a contact boundary surface, wherein the detector is arranged such that during operation of the device the sensing beam on a path from the radiation source providing the sensing beam to the detector is at least once reflected at the contact boundary surface of the sensing window by total internal reflection once the contact boundary surface of the sensing window is in contact with air, and a controller communicating with the radiation source providing the operating beam and with a detector and being operable to influence operation of the radiation source providing the operating beam responsive to the sensing beam detected at the detector.

Eye safety is achieved by preventing hazardous electromagnetic radiation of the operating beam from radiating out of the device as long as at least part of the sensing window is in contact with air only. As soon as any other material than air, e.g. a person's skin is in contact with sections of the sensing window total internal reflection at the contact boundary surface of the sensing window is disturbed and less light of the sensing beam is incident on the detector. The controller as a response to the change in the amount of light incident on the detector influences operation of the radiation source providing the operating beam and prevents hazardous radiation from exiting the housing of the device.

It is a further aspect of the invention to provide an electrical household appliance comprising a light emitting device according to the first aspect of the invention.

An example for an electrical household appliance under a further aspect of the invention is an electromagnetic hair removal device.

Under another aspect of the invention a method for emission of light is provided comprising the steps generating at least one operating beam of electromagnetic radiation, providing a housing being intransparent for the operating beam having an output opening, wherein the operating beam is generated in the housing, and wherein the operating beam and the output opening are arranged such that during operation of the device the operating beam may exit the housing through the output opening, generating at least one sensing beam of electromagnetic radiation, detecting the sensing beam, wherein the sensing window is detected after total internal reflection at a contact boundary surface of a sensing window once the contact boundary surface of the sensing window is in contact with air, and controlling generation of the operating beam responsive to the detection of the sensing beam.

DETAILED DESCRIPTION OF THE INVENTION

Under an aspect of the invention the radiation source for electromagnetic radiation providing the operating beam and the radiation source for electromagnetic radiation providing the sensing beam may be one and the same emitting source.

Under an alternative aspect of the invention the radiation source providing the operating beam and the radiation source providing the sensing beam may be separate from each other, i.e. at least two separate emitting sources for electromagnetic radiation.

In case the radiation source for the operating beam and the radiation source for the sensing beam are provided by a single source for electromagnetic radiation the radiation source under an aspect of the invention may comprise a beam splitter in order to split the radiation emitted from the actual emitter into a sensing beam and an operating beam.

Under another aspect of the invention, wherein the sensing beam as well as the operating beam are provided by a single source the radiation source may comprise a moveable or switchable mirror.

Under an aspect of the invention the radiation source for the operating beam may be a laser.

Under another aspect of the invention the second radiation source for the sensing beam may be a light emitting diode.

It is a further aspect of the invention that the second radiation source for the sensing beam may be a laser diode.

Under an aspect of the invention the detector may be any kind of radiation sensitive element providing an electric output signal. Under an aspect the detector may be a semiconductor detector. Examples for semiconductor detectors are photodiodes and phototransistors. While under an aspect of the invention the detector may be a single pixel device it may be another aspect of the invention that the detector is a device having a plurality of pixels. For example a CCD-camera or a CMOS-camera may be used as a detector having a plurality of pixels. Under a further aspect of the invention the detector may be a skin detector.

Under an aspect of the invention the sensing window provides a light guide for the sensing beam during operation of the device. The light guide may enhance homogeneity of the operating beam.

It is an aspect of the invention that the sensing window may provide an entry boundary surface for the sensing beam, wherein the entry boundary surface for the sensing beam with respect to the contact boundary surface and the angle of incidence of the sensing beam at the entry boundary surface are arranged such that during operation of the device the sensing beam experiences a total internal reflection at the contact boundary surface once the contact boundary surface is in contact with air.

Total internal reflection at the refractive index may occur at the boundary surface between a medium having a higher refractive index $n_h$ than $n_l$ of the material on the other side of the boundary surface for angles of incidence of a light beam being incident on the boundary surface from the direction of the medium having the higher refractive index $n_h$ being larger than the critical angle $\alpha_{crit}$. The critical angle $\alpha_{crit}$ can be determined as $$\alpha_{crit} = Arcusinus\left(\frac{n_l}{n_h}\right).$$

Once the contact boundary surface of the sensing window is brought into contact with tissue, for example skin, the critical angle for the total internal reflection to occur drastically changes, as for example skin has a refractive index of $n_{skin}$ of approximately 1.4, which is considerably higher than the refractive index of air such if the angle of incidence of the sensing beam at the contact boundary surface is chosen correctly the total internal reflection vanishes once the contact boundary surface is brought into contact with tissue, e.g. skin.

Accordingly under an aspect of the invention the sensing window may provide an entry boundary surface for the sensing beam, wherein the entry boundary surface for the sensing beam with respect to the contact boundary surface and the angle of incidence of the sensing beam at the entry boundary surface may be arranged such that during operation of the device the sensing beam does not experience a total internal reflection at a contact boundary surface once the contact boundary surface is in contact with skin.

Under an aspect of the invention the sensing window may be made of poly-methylmethacrylate, which is frequently denoted as PMMA, having a refractive index of approximately 1.49.

The invention may prevent hazardous radiation from emitting from the housing in which the radiation source providing the operating beam is located unless the light emitting device is operated under safe conditions. It may be considered safe once the output opening of the housing accommodating the radiation source providing the operating beam is in contact with skin such that the housing accommodating the radiation source providing the operating beam together with the skin forms a closed volume from which leaking of eye hazardous radiation is unlikely to occur.

Thus under an aspect of the invention the sensing window may be located adjacent to the output opening of the housing. It may be likely if the sensing window and the output opening of the housing are located adjacent to each other that once the sensing window is in contact with tissue the output opening will also be in contact with or covered by tissue preventing hazardous radiation from leaking out of the enclosed volume formed by the housing and the skin.

It is another aspect of the invention that the sensing window may be located in the output opening of the housing, wherein the sensing window is made of a material being transparent for the operating beam as well as for the sensing beam during operation of the device, and wherein during operation of the device the operating beam may exit the housing through the sensing window.

The area of the output opening of the housing for the operating beam and the area of the sensing beam at least partly being identical or overlapping may help to reliably predict from the condition of the sensing beam at the detector, i.e. its power level, whether the opening of the housing is in contact with a tissue or not.

Under an aspect of the invention the controller communicating with the radiation source providing the operating beam and with the detector may be operable to enhance the output power of the radiation source providing the operating beam once it is detected at the detector that no internal reflection at the contact boundary surface occurs, i.e. that the contact boundary surface of the sensing window is in contact with tissue.

It is another aspect of the invention that the controller communicating with the radiation source providing the operating beam and with the detector may be operable to switch off the operating beam once it is detected at the detector that the sensing window is not in contact with tissue, i.e. total internal reflection of the sensing beam at the contact boundary surface occurs leading to a high power level of the sensing beam being incident on the detector.

Under an aspect of the invention the radiation source providing the operating beam and the radiation source providing the sensing beam may be arranged such that the operating beam has a first wavelength and the sensing beam has a second wavelength, wherein the first wavelength and the second wavelength are different from each other, and wherein the detector is only sensitive for the second wavelength of the sensing beam.

Providing sensitivity of the detector only for the second wavelength of the sensing beam leads to an effective suppression of all other radiation and thus a background free or a background reduced measurement of the sensing beam at the detector.

Under an aspect of the invention the at least one second radiation source for the sensing beam and the least one detector are located on opposing sides of the sensing window.

Under another aspect of the invention the at least one radiation source providing the sensing beam and the at least one detector may be located on an identical side of the sensing window, wherein on the side of the sensing window opposing the second radiation source for the sensing beam and the detector a reflector is located for deflecting the sensing beam.

Provision of a reflector in the beam path of the sensing beam enables a beam shaping of the beam at the contact boundary surface of the sensing window. It is thus another aspect of the present invention that the reflector may be designed such that the sensing beam reflected covers an extended area on the contact boundary surface of the sensing window.

Under another aspect of the invention the reflector may be designed such that the sensing beam reflected covers an area on the contact boundary surface being identical to or smaller than the cross-sectional area of the operating beam exiting the housing through the sensing window. Under an aspect of the invention the reflector may be designed such that the sensing beam reflected covers an area on the contact boundary surface which amounts to at least 60% of the cross-sectional area of the operating beam exiting the housing through the sensing window.

Once a large share of the cross-sectional area of the operating beam at the contact boundary surface is covered by the sensing beam residuals of dust, liquids or soil on the area monitored do less severely influence the overall signal to be detected at the detector. I.e. by monitoring a large area, small areas in which total internal reflection is lost by undesired effects, are less significant compared to cases in which the area of the contact boundary surface monitored is smaller. Furthermore once the area of the contact boundary surface of the sensing window being covered by the sensing beam is almost identical to the cross-sectional area of the operating beam exiting the sensing window, it may prevent that only a partial covering of the sensing window by tissue may be detected as a full coverage.

Under an aspect of the invention the reflector may be provided by a reflector being external to the sensing window.

Under another aspect of the invention the reflector may be provided by a reflecting coating of a boundary surface of the sensing window.

Under a further aspect of the invention the reflector may be provided by total internal reflection at a boundary surface of the sensing window.

Under an aspect of the invention the sensing window in a cross-sectional plane parallel to the contact boundary surface may have a saw tooth-like shape.

A saw tooth-like cross-section in a plane parallel to the contact boundary surface may form a reflector having retroreflector-like characteristics in one dimension.

It is another aspect of the invention that the boundary surface of the sensing window may comprise a plurality of pairs of surface sections forming an angle with each other, which ensures retroreflecting properties of the boundary surface for at least part of the sensing beam. Under another aspect the sensing window may comprise a plurality of pairs of surface sections forming an angle in a range from about 75° to about 90° with each other.

Under an aspect of the invention a plurality of sensing beams may be provided by a plurality of radiation sources providing the sensing beams.

By using a plurality of sensing beams being incident on the contact boundary surface of the sensing window, multiple spots of the sensing window at different areas of the sensing window may be monitored simultaneously.

Under an aspect of the invention two radiation sources providing two sensing beams and one detector are located on an identical side of the sensing window, wherein on the side of the sensing window opposing the radiation sources providing the sensing beam and the detector a reflector may be located.

Under another aspect of the invention calibration of the detector may be performed by measuring the sensing beam without contact of the contact boundary surface of the sensing window to skin. A high measurement value may be the "no-contact" reference. The measurement value will be reduced when skin contact is applied and once the value drops below a predetermined threshold the controller will identify that skin contact is established. Once the measured value increases above the given threshold, the detector identifies that skin contact is lost.

Under an aspect of the invention calibration may be performed only once after manufacturing of the light emitting device.

Under an alternative aspect an automatic calibration may be implemented, for example every time the device is switched on. The device then always detects and accepts the maximum measured value as the current "no-contact" reference.

Under an aspect in case two or more sensing beams are used alternately it may be required that the power levels detected at the detector both need to drop below the predetermined threshold in order to identify skin contact. Alternatively it may be sufficient to identify skin contact when only one of the power levels detected at the detector drops below the threshold value.

Under an aspect of the invention the housing may be of color material absorbing scattered light from the sensing beam.

Under an aspect of the invention the radiation source providing the sensing beam may be operated in two phases: radiation source on and radiation source off. The measured signal when the radiation source is switched off may be subtracted from the signal when the radiation source is switched on. This way, any effect of background light may be eliminated.

Under a further aspect of the invention the controller may be a hard wired electronic circuit.

In the following particular embodiments of light emitting devices are described with reference to the accompanying figures as example embodiments of aspects of the invention as laid out above. Throughout the figures identical reference numbers do denote identical parts.

Figure 1:
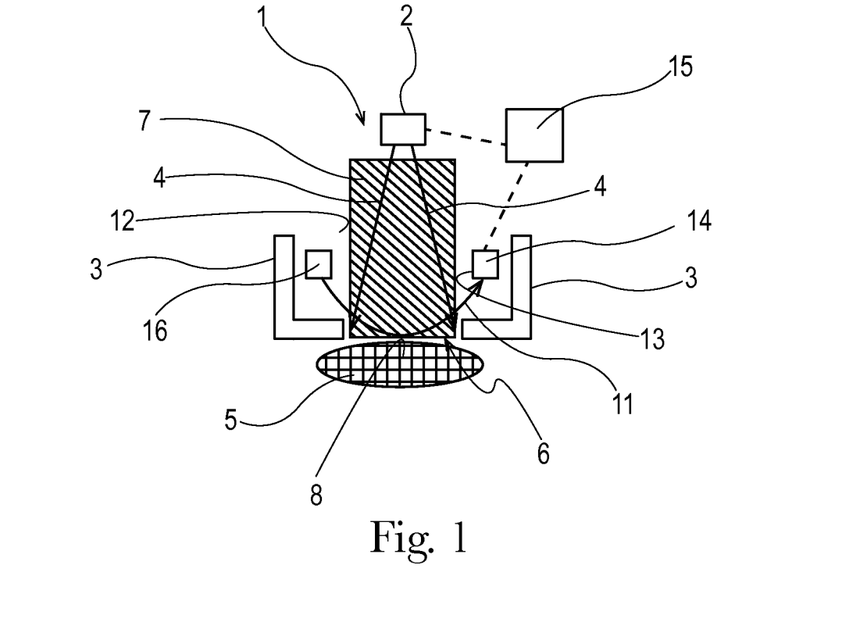
FIG. 1 shows an example of a schematic cross-sectional view of the front part of a laser device.

FIG. 1 shows a schematic view of a light emitting device, which here is formed as a laser device 1 in order to demonstrate the purpose and functionality of aspects of the present invention.

A laser source, namely a high power diode laser 2, is located in a housing 3. In order to enable an effective management on hair growth on skin the laser source 2 may be a class 1 to 4 laser source according to the laser safety standard ISO EN 60825-1/2007.

During operation of the device 1 the laser 2 provides an operating beam 4 which serves to manage hair growth on a person's skin 5. The laser 2 forms the radiation source for electromagnetic radiation providing the operating beam in the sense of the present application.

The operating beam 4 may exit the housing 3 through an output opening 6. As schematically depicted in FIG. 1 the laser device 1 during operation is placed on a person's skin 5 such that the operating beam 4 may enter the skin 5 through the output opening 6 of the housing 3.

Unless prevented by the device according to an aspect of the invention the operating beam 4 would even exit the housing 3 when the device 1 is removed from the skin 5.

Under an aspect of the invention the light emitting device prevents emission of eye hazardous radiation from the operating beam 4 from the housing 3 once the output opening 6 is not in contact with the skin 5.

In the embodiment depicted in FIG. 1 a sensing window 7 is located in the housing 3 extending such that it is also located in the output opening 6 of the housing 3 providing an exit window for the operating beam 4. The sensing window 7 comprises a contact boundary surface 8 which during operation of the device 1 may be brought into contact with the skin 5.

Embodiments of the invention aim at either reducing the output power of the laser source 2 or switching it entirely off once during operation the contact boundary surface 8 of the sensing window 7 is not in contact with the skin 5.

The skin 5 to be treated is used as a barrier for the light and during operation can be considered as part of the protective system as the skin 5 when in contact with the contact boundary surface 8 prevents light of the operating beam 4 from leaking out of the housing 3.

The minimum contact requirements according to an aspect of the invention are determined by device safety on the one hand and device handling on the other hand. The larger the required contact boundary surface 8 of the sensing window 7 is the higher the safety level is as less space is left for laser light 4 to propagate into the surrounding environment. On the other hand, larger contact area requirement may impede the device handling, i.e. a user must ensure that a larger area of the contact boundary surface 8 is in contact with skin during use, thus increasing the care the user will have to take in order to fulfill the contact requirement. This may be especially difficult on bony areas such as the shin. Reducing the required contact area in general may increase the requirements for further measures in order to guarantee eye safety, e.g. a diffuser placed in the beam path of the operating beam 4. The diffuser may serve in order to reduce the spatial coherence and reduce the radiance of the operating beam 4 exiting the housing 3 and thus reduce eye hazard of the beam 4.

Figure 11:
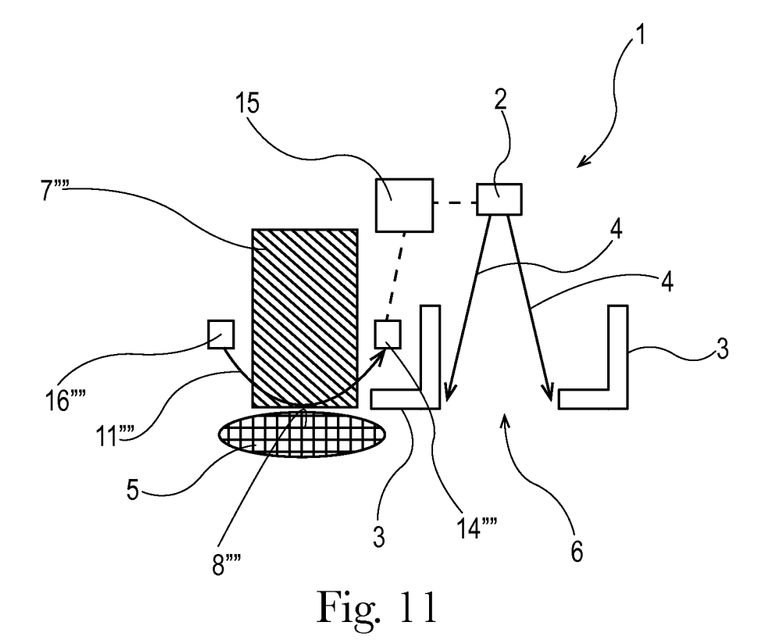
FIG. 11 shows a schematic side view of a laser device.

While in the embodiment depicted in FIG. 1 the sensing window 7 is located within the output opening 6 of the housing 3 there may be embodiments like for example the one shown in FIG. 11, wherein the sensing window 7"" is located adjacent to the output opening 6 of the housing 3.

Referring further to FIG. 1 operational safety of the device 1 is ensured by usage of a sensing beam 11. In the housing 3 a second radiation source 16 for electromagnetic radiation provides the sensing beam 11. The sensing beam 11 enters the rectangular sensing window 7 through an entry boundary surface 12 of the sensing window 7. The angle of incidence of the sensing beam 11 at the entry boundary surface 12 is chosen such that the sensing beam at the contact boundary surface 8 experiences a total internal reflection once the contact boundary surface 8 of the sensing window 7 is in contact with air. Once total internal reflection at the contact boundary surface 8 occurs the sensing beam 11 will exit the sensing window 7 through an output boundary surface 13 and is then incident on a detector 14 detecting the power level of the sensing beam 11.

The detector 14 is in communication with a controller 15 which in turn is in communication with the radiation source 2 providing the operating beam 4. The controller 15 monitors the power level of the sensing beam 11 detected by the detector 14. Once the total internal reflection experienced by the sensing beam 11 at the contact boundary surface 8 is disturbed, e.g. by bringing the contact boundary surface 8 of the sensing window 7 in contact with skin 5, the power level of the sensing beam 11 detected at the detector 14 drops. Once the power level detected at the detector 14 rises above a certain threshold, the controller 15 in the embodiment shown in FIG. 1 will switch off the radiation source 2 providing the operating beam and thus prevents any radiation of the operating beam from leaking out of the housing 3.

Figure 2A:
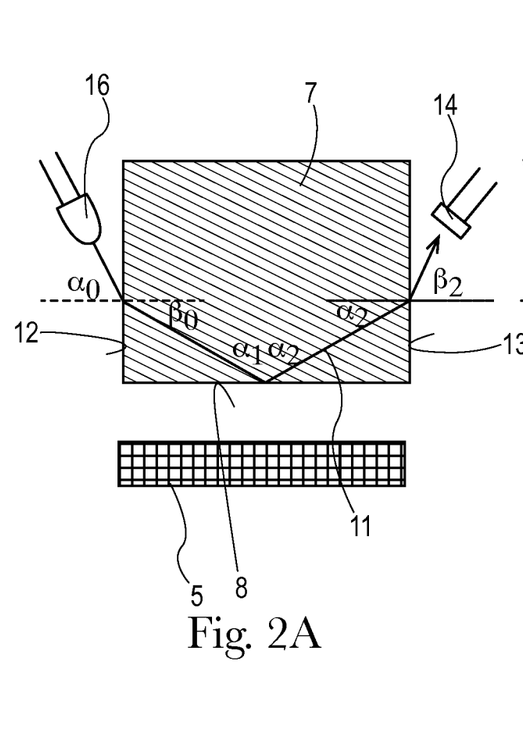
FIG. 2 shows a schematic cross-sectional view of a part of a laser device.

The functionality of the embodiment of FIG. 1 is now described in more detail with reference to FIGS. 2a) and b). Total internal reflection of the sensing beam 11 at the contact boundary surface 8 of the sensing window 7 occurs once the angle of incidence $\alpha_1$ at the contact boundary surface 8 is larger than the critical angle $\alpha_{crit}$ for the total internal reflection. In the embodiment depicted the sensing window 7 is made of PMMA having a refractive index of approximately $n_{PMMA}=1.49$ such that once the contact boundary surface 8 is in contact with air the critical angle of total internal reflection is $\alpha_{crit}=42°$. Accordingly in the embodiments depicted the angle of incidence $\alpha 0$ of the sensing beam 11 at the entry boundary surface 12 is chosen such that the angle of incidence $\alpha_1$ at the contact boundary surface 8 is about 50°. Under these conditions the angle of incidence $\alpha_2$ of the sensing beam 11 at the exit boundary surface 13 of the sensing window 7 amounts to 40° such that the angle of incidence $\alpha_2$ at the exit boundary surface 13 is smaller than the critical angle $\alpha_{crit}$ avoiding any total internal reflection from the exit boundary surface 13.

Figure 2B:
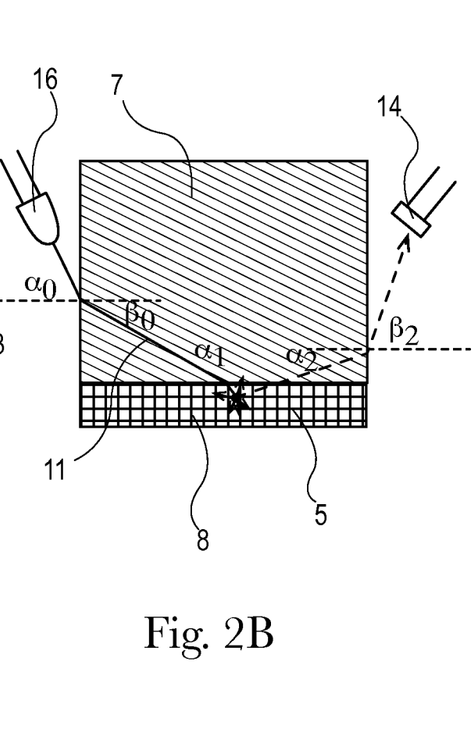

FIG. 2b) shows a situation in which the contact boundary surface 8 is in contact with skin 5 having a refractive index $n_{skin}$ of approximately 1.4 leading to a critical angle for total internal reflection of $\alpha_{crit}=69°$. As the angle of incidence $\alpha_1$ is independent from any material brought into contact with the contact boundary surface 8 of the sensing window 7 in the situation of FIG. 2b) the angle of incidence $\alpha_1$ at the contact boundary surface 8 is smaller than the critical angle of the boundary surface 8 between the sensing window 7 of PMMA and skin 5 brought into contact with the contact boundary surface 8.

As hardly any light of the sensing beam 11 will fall onto detector 14 in the situation depicted in FIG. 2b), wherein the skin 5 is in contact with the contact boundary surface 8, the power level detected at the detector 14 will fall below a preset threshold value, enabling switching-on of the laser source 2 for the operating beam by the controller.

While the principle for switching the sensing beam by a change in the total internal reflection of the sensing beam 11 at a contact boundary surface 8 is the same for the embodiments depicted in FIGS. 3 to 11 those embodiments differ from the embodiment depicted schematically with reference to FIGS. 1 and 2 in that the overall beam path of the sensing beam 11 is different.

While most of the embodiments described in detail below will be described to have at least two distinct radiation sources, i.e. at least one first radiation source for providing the operating beam and one second radiation source for providing the sensing beam it is apparent to a person skilled in the art that embodiments are feasible in which a single radiation source is used for providing both the operating beam as well as the sensing beam.

Figure 12:
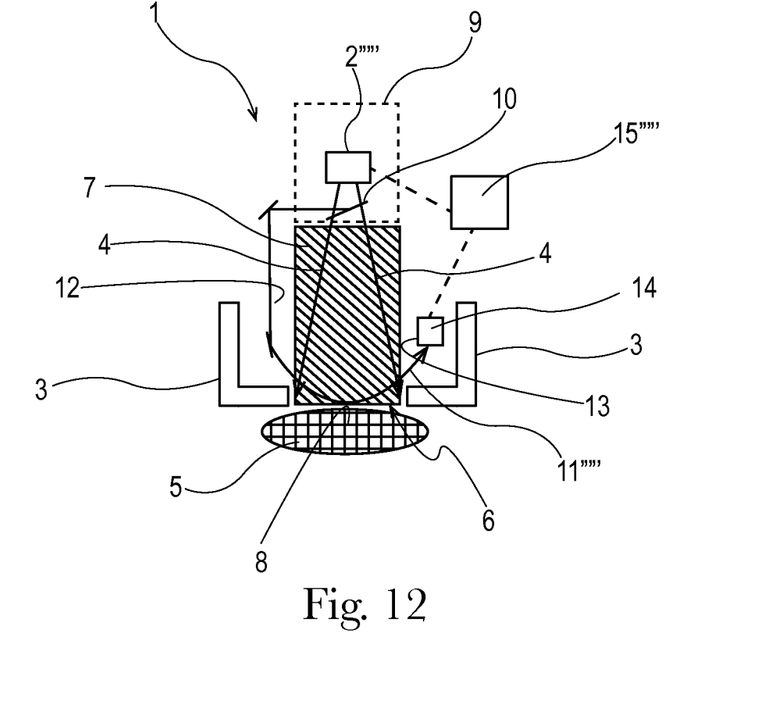
FIG. 12 shows a schematic side view of a laser device.

An embodiment having a single source for the operating beam as well as for the sensing beam is schematically depicted in FIG. 12. In this embodiment the radiation source 9 is formed of a semi-conductor laser 2'''' and a movable mirror 10. The radiation emitted from the laser 2'''' is either reflected by the mirror 10 to form a sensing beam 11'''' or it is transmitted in order to form an operating beam 4. When the mirror 10 is in a position as depicted in FIG. 12 it reflects the beam into the sensing beam's beam path. When the mirror is retracted the light emitted from the laser source 2'''' is emitted as the operating beam 4.

As explained before with reference to FIGS. 2a) and b) the sensing beam 11'''' is incident on an entry boundary surface 12 of the sensing window 7 such that the sensing beam 11'''' experiences a total internal reflection at the contact boundary surface 8 of the sensing window 7 once the sensing window 7 is in contact with air. After reflection from the contact boundary surface 8 the sensing beam 11'''' exits the sensing window 7 through an exit boundary surface 13 of the sensing window 7. The sensing beam 11'''' exiting the sensing window 7 is incident on a detector 14 detecting the power of the sensing beam 11''''. The detector 14 is in communication with a controller 15'''' which in turn is in communication with the semi-conductor laser 2'''' and with a drive operating the mirror 10. Once the total internal reflection of the sensing beam 11'''' at the contact boundary surface 8 of the sensing window 7 is disturbed, for example once the contact boundary surface 8 is in contact with skin, the power level of the sensing beam 11'''' at the detector 14 drops. Once the power level falls below a certain threshold the controller 15'''', which is monitoring the power of the sensing beam 11'''' at the detector 14, will urge the drive operating the mirror 10 to retract the mirror 10 such that the operating beam 4 may be emitted from the housing.

In an alternative embodiment the mirror 10 may be a switchable mirror avoiding a mechanical movement of the mirror.

While in the embodiment depicted in FIGS. 1, 2 and 11 the radiation source 16 providing the sensing beam 11 and the detector 14 are located on opposing sides 12, 13 of the sensing window 7 in the embodiments of FIGS. 3 to 9 at least one radiation source providing the sensing beam 11 and at least one detector for detecting the sensing beam after total internal reflection at the contact boundary surface 8 of the sensing window 7 are located on the same side of the sensing window 7.

What the embodiments of FIGS. 3 to 9 thus have in common is that on the opposing side of the side of the sensing window 7 at which the radiation source and the detector are located a reflector is located deflecting the sensing beam in order to complete the beam path of the sensing beam.

Figure 3:
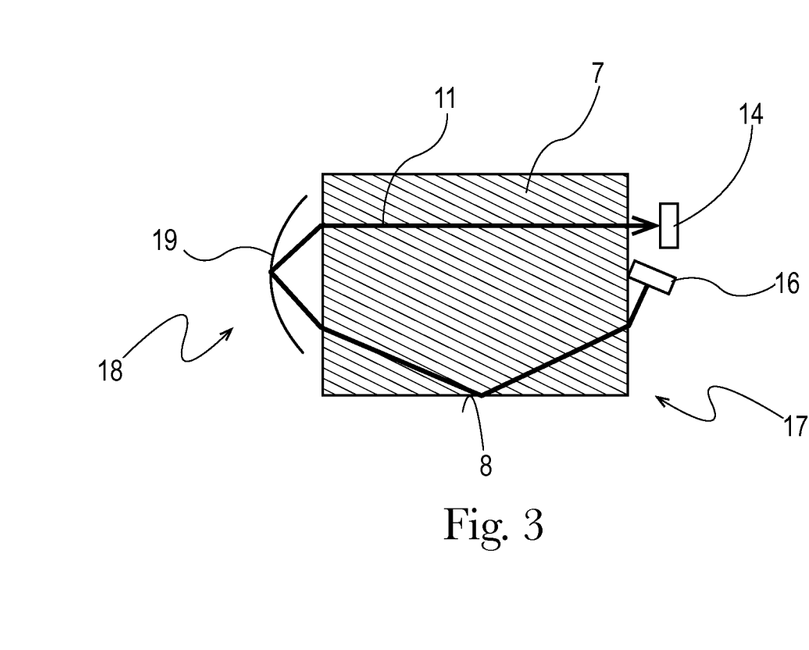
FIG. 3 shows a schematic side view of a part of a laser device.

In the embodiment depicted in FIG. 3 there is on a first side 17 of the sensing window 7 a light emitting diode 16 as the radiation source providing the sensing beam 11 as well as a detector 14 for detecting the power level of the sensing beam 11 after total internal reflection at a contact boundary surface 8 of the sensing window 7. On the second opposite side 18 of the sensing window 7 a concave mirror 19 as a reflector is located, which not only redirects the sensing beam 11, but also leads to a beam shaping of the sensing beam 11.

The beam path of the sensing beam 11 under a condition in which total internal reflection occurs at the contact boundary surface 8 of the sensing window 7 is briefly explained as follows: the sensing beam 11 is emitted from the light emitting diode 16 in a direction towards the boundary surface 8, it enters the sensing window 7 and is totally internally reflected at the contact boundary surface 8. The sensing beam 11 then exits the window 7 on the opposing side 18 where it is deflected by the mirror 19 which focuses the sensing beam 11 onto the detector 14. The sensing beam then enters the sensing window 7 again, passes the sensing window 7, and exits the window 7 before being detected by the detector 14. The mirror 19 focuses the sensing beam 11 such that the illumination on the contact boundary surface is imaged onto the detector.

From the cross-sectional view of FIG. 3 it is apparent that the mirror in this embodiment is curved in one dimension. In the embodiment depicted in FIG. 3 the mirror 19 is a cylindrical mirror.

Figure 4:
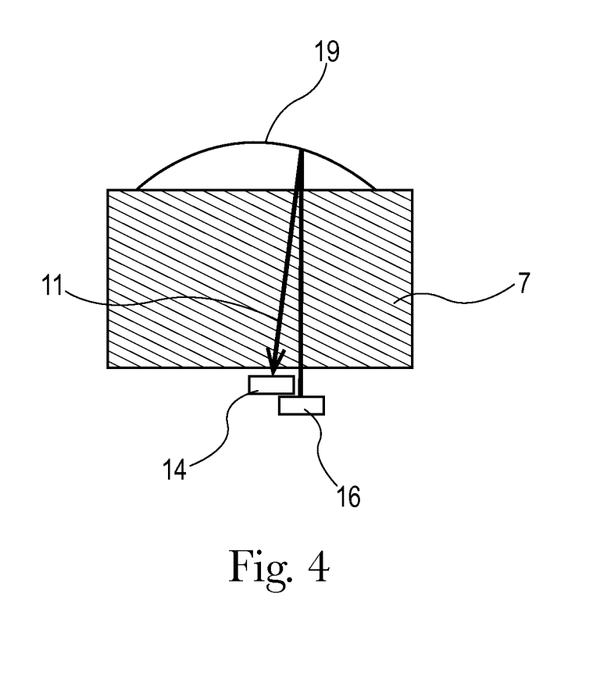
FIG. 4 shows a schematic top view of the laser device of FIG. 3.

FIG. 4 shows a top view of an embodiment which is highly similar to the one of FIG. 3. However, the mirror 19 comprises a curvature in two dimensions.

Figure 5:
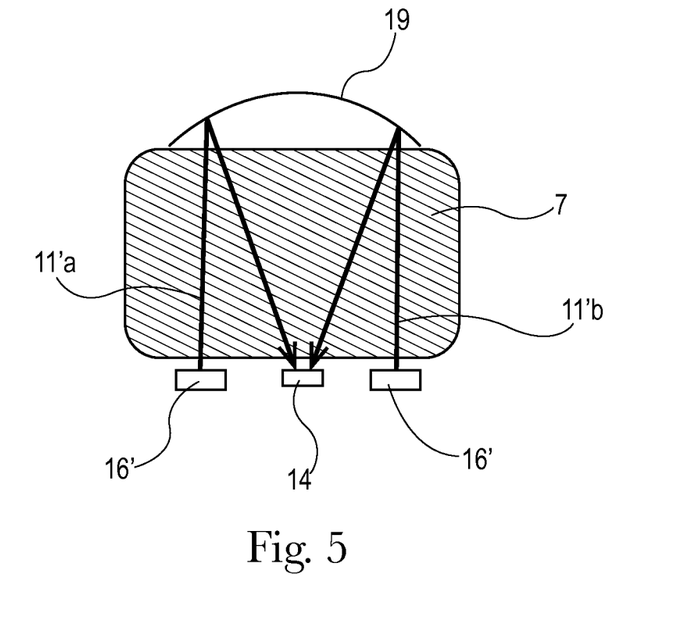
FIG. 5 shows a schematic top view of a part of a laser device.

FIG. 5 shows another embodiment which is developed from the embodiment of FIG. 4 but uses two or more distinct second radiation sources 16' providing two or more sensing beams 11'a, 11'b. Two different light emitting diodes 16' are used to illuminate different parts of the contact boundary area of the sensing window 7.

Under an aspect of the invention the light emitting diodes 16' may be activated alternately and the power levels of the two beams 11'a and 11'b can be detected independently from each other at the detector 14. The signaling of an established contact between the contact boundary surface and skin may be established once only one of the sensing beams 11'a and 11'b drops below the required power level.

Under an alternative aspect of the invention both power signals from the two sensing beams 11'a and 11'b may have to fulfill a certain power requirement together in order to signalize an established contact.

The embodiments of FIGS. 6, 7, 8 and 9, do all realize a reflector being integrated into the sensing window 7'' and 7''' on a side of the sensing window opposing the light source 16 providing the sensing beam 11 and the detector 14.

Figure 6:
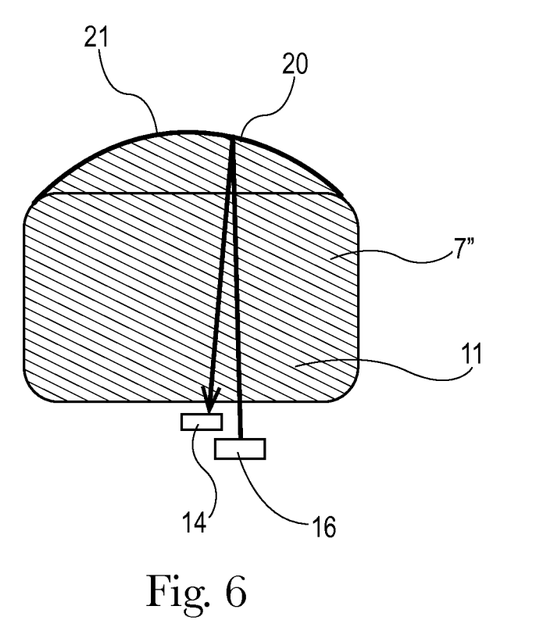
FIG. 6 shows a schematic top view of a further aspect of a part of a laser device.

In the embodiment of FIG. 6 the sensing window 7'' at its side opposing the light emitting diode 16 and the detector 14 does have a convex shape while the surface 20 of the convex area is coated by a reflecting metal coating 21. The mirror thus formed at the surface 20 of the sensing window 7'' in principle has the same functionality as the external mirror 19 as shown for example in the embodiment of FIG. 5.

In the embodiments shown in FIGS. 7 to 10 the reflector is formed by the boundary surface 23 of the sensing window 7''' itself. One side 22 of the sensing window 7''' is shaped such that total internal reflection at the boundary surface 23 between the sensing window 7''' and air on this side 22 occurs. As this side 22 of the sensing window 7''' is only in contact with air the conditions for total internal reflection will always be fulfilled given an appropriate design of the shape of the boundary surface 23 as well as the beam paths of the sensing beams 11''', 11'''a, 11'''b. This avoids an additional reflecting coating of the sensing window 7'''.

In the embodiments according to FIG. 7 and FIGS. 8 to 10, respectively the beam paths of the sensing beams 11, 11'''a, 11'''b run from the light emitting diodes 16, 16''' via a total internal reflection at the contact boundary surface 8 and a further total internal reflection at the boundary surface 23 of the sensing window 7''' to the detector 14.

Figure 7:
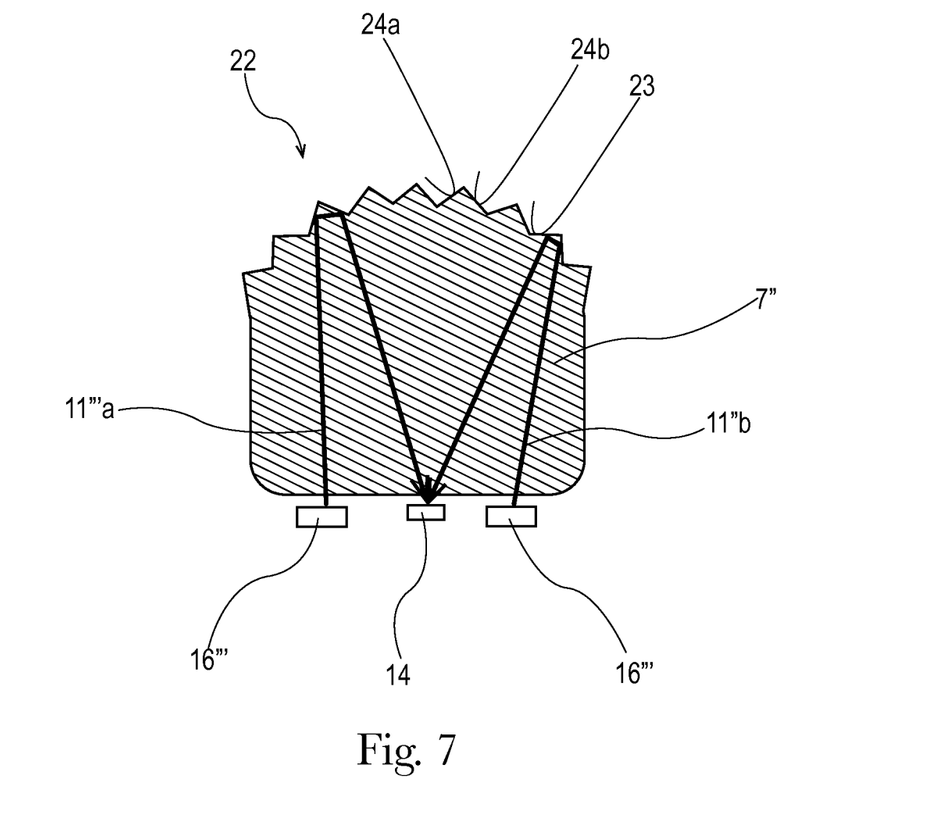
FIG. 7 shows a schematic top view of a part of a laser device.
Figure 8:
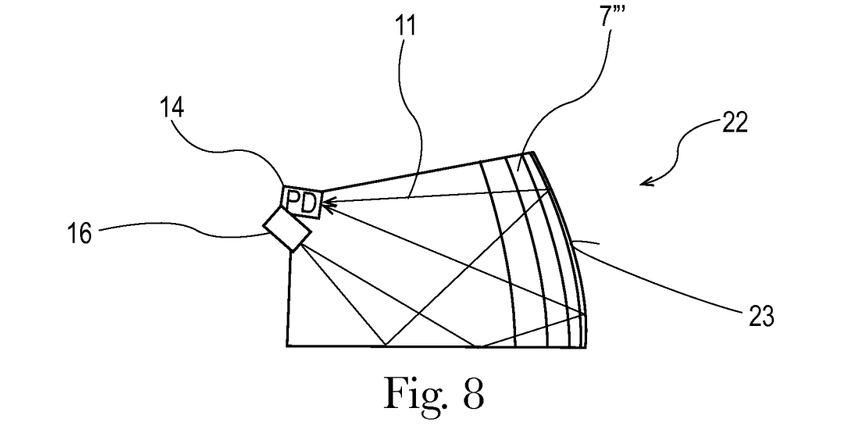
FIG. 8 shows a schematic side view of a part of a laser device.
Figure 9:
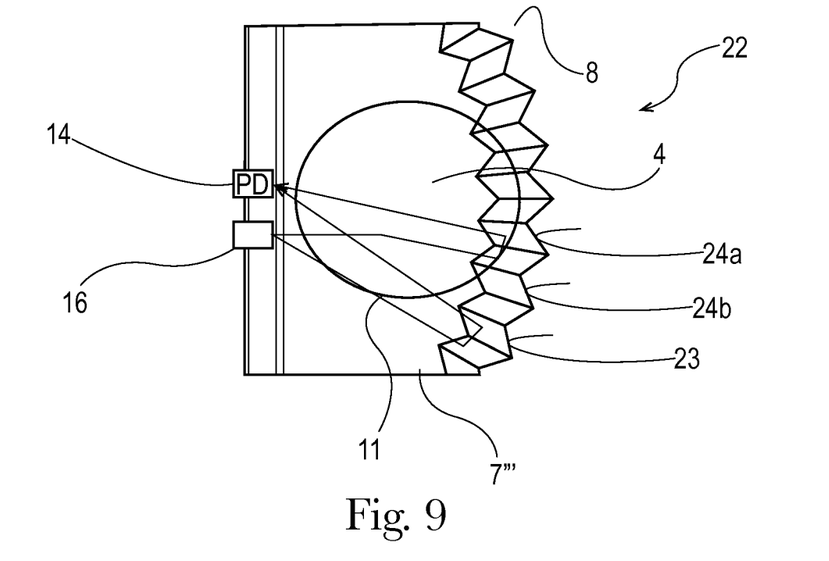
FIG. 9 shows a schematic top view of the laser device according to FIG. 8.
Figure 10:
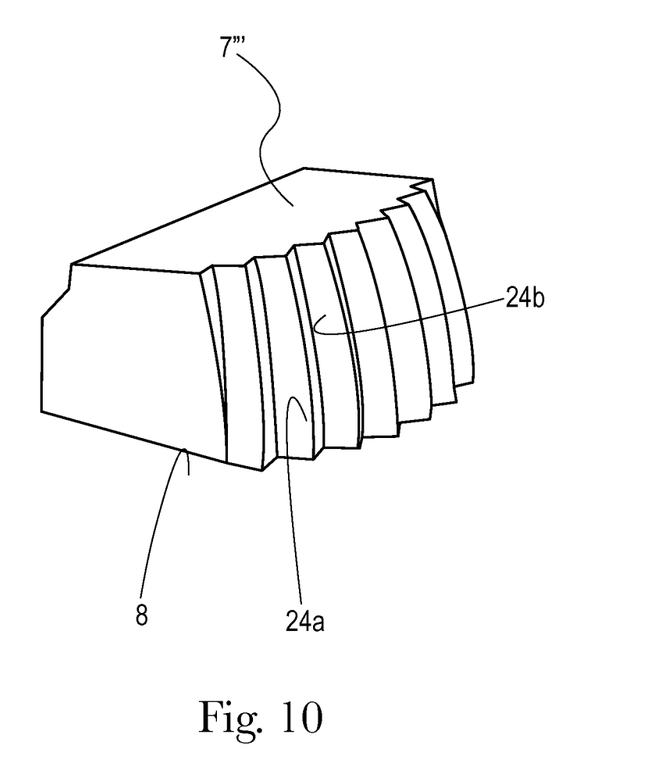
FIG. 10 shows a perspective view of a sensing window according to FIGS. 8 and 9.

In the embodiment shown in FIG. 7 as well in the embodiment of FIGS. 8 to 10 the boundary surface 23 at the side 22 of the sensing window 7''' providing the reflector has a saw-tooth-like structure, which is designed such that at least in one direction a focusing of the sensing beam 11, 11'''a, 11'''b onto the detectors 14 occurs by total internal reflection. The shape has retroreflecting as well as focusing characteristics.

The boundary surface 23 is thus formed of a plurality of pairs of surface sections 24a, 24b being perpendicular or nearly perpendicular to each other when viewed in a cross-sectional plane being parallel to the radius of curvature of the boundary surface 23.

Under an aspect of the invention the sensing window 7''' may be injection molded or milled out of any optical grade material, such as glass, polycarbonate or PMMA.

The shape of the sensing window or light guide and of the saw-tooth structure is dependent on the refractive index of the material. Thus, the shape may be adjusted according to the material used.

As described before with reference to FIG. 5 also the embodiment of FIG. 7 comprises two light emitting diodes 16''' providing two distinct sensing beams 11'''a and 11'''b. Two different light emitting diodes 16''' are used to illuminate different parts of the contact boundary area of the sensing window 7'''.

The light emitting diodes 16''' may be activated alternately and the power levels of the two beams 11'''a and 11'''b can be detected independently from each other at the detector 14. In the embodiment depicted in FIG. 7 both power signals at the detector 14 from the two sensing beams 11'a and 11'b have to fulfill a certain power requirement together in order to signalize an established contact. This way it may be avoided that only covering part of the contact boundary surface by skin may already lead to an emission of light of the operating beam from the housing.

Alternatively and as depicted according to the embodiment of FIGS. 8 and 9 the light emitting device may only comprise a single source 16 and a single detector 14.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

REFERENCE SIGNS

1 Device
2, 2' Laser source
3 Housing
4, 4' Operating beam
5 Skin
6 Output opening
7, 7', 7", 7''' Sensing window
8 Contact boundary surface
9 Radiation source
10 Beam splitter
11, 11'a, 11'b Sensing beam
12 Entry boundary surface
13 Exit boundary surface
14 Detector
15, 15' Controller
16, 16' Light emitting diode
17 First side of sensing window
18, 22 Second side of sensing window
19 Concave mirror
20 Boundary surface
21 Reflecting metal coating
23 Boundary surface

What is claimed is:

1. A light emitting device comprising
at least one operating beam radiation source for electromagnetic radiation providing at least one operating beam during operation of the device,
a housing being intransparent for the operating beam and having an output opening,
wherein the operating beam radiation source providing the operating beam is located in the housing, and
wherein the operating beam radiation source providing the operating beam and the output opening are both arranged such that during operation of the device the operating beam is configured to exit the housing through the output opening,
at least one sensing beam radiation source for electromagnetic radiation providing at least one sensing beam during operation of the device, at least one detector for detecting the sensing beam,
at least one sensing window having a contact boundary surface, wherein the detector is arranged such that during operation of the device the sensing beam on a path from the sensing beam radiation source to the detector is at least once reflected at the contact boundary surface of the sensing window by total internal reflection once the contact boundary surface of the sensing window is in contact with air, and
a controller communicating with the operating beam radiation source and with the detector and the controller being operable to influence operation of the operating beam radiation source in a manner that is responsive to the sensing beam detected at the detector,
wherein the sensing beam radiation source providing the sensing beam and the at least one detector are located on an identical side of the sensing window, wherein on the side of the sensing window opposing the sensing beam radiation source and the detector a reflector is located; and wherein the sensing window is positioned in a cross-sectional plane parallel to the contact boundary surface; the contact boundary surface has a saw tooth-like shape and is configured to engage a user's skin during use,
wherein the sensing window is located in the output opening of the housing, wherein the sensing window is made of a material being transparent for the operating beam and for the sensing beam, and wherein during operation the device the operating beam is configured to exit the housing through the sensing window; wherein the operating beam emitted by the operating beam radiation source has a first wavelength, and wherein the sensing beam emitted by the sensing beam radiation source has a second wavelength; and wherein the detector is sensitive only to the second wavelength of the sensing beam.

2. The light emitting device (1) according to claim 1, wherein the sensing window (7) provides a light guide for the sensing beam (11) during operation of the device (1).

3. The light emitting device (1) according to claim 1 or 2, wherein the sensing window (7) provides an entry boundary surface (12) for the sensing beam (11), wherein the entry boundary surface (12) for the sensing beam (11) with respect to the contact boundary surface (8) and the angle of incidence of $\alpha_1$ the sensing beam (11) at the entry boundary surface (12) are arranged such that during operation of the device (1) the sensing beam (11) experiences a total internal reflection at the contact boundary surface (8) once the contact boundary surface (8) is in contact with air.

4. The light emitting device (1) according to claim 3, wherein the sensing window (7) provides an entry boundary surface (12) for the sensing beam (11),
wherein the entry boundary surface (12) for the sensing beam (11) with respect to the contact boundary surface (8) and the angle of incidence of the sensing beam (11) at the entry boundary surface (12) are arranged such that during operation of the device (1) the sensing beam (11) does not experience a total internal reflection at the contact boundary surface (8) once the contact boundary surface (8) is in contact with skin (5).

5. The light emitting device (1) according to claim 1, wherein the reflector is provided by a reflecting coating (21) on a boundary surface (20) of the sensing window (7).

6. The light emitting device (1) according to claim 1, wherein the reflector is provided by total internal reflection at a boundary surface (23) of the sensing window (7).

7. The light emitting device (1) according to claim 1, wherein the boundary surface (23) of the sensing window (7''') comprises a plurality of pairs of surface sections (24a, 24b) forming an angle with each other, which ensures retroreflecting properties of the boundary surface (23) for at least part of the sensing beam.

8. The light emitting device (1) according to claim 7, wherein a plurality of sensing beams (11) is provided by a plurality of second radiation sources (16').

9. The light emitting device (1) according to claim 8, wherein two radiation sources (16') providing two sensing beams (11) and one detector (14) are located on an identical side of the sensing window (7), wherein on a side of the sensing window (7) opposing the radiation sources (16') providing the sensing beams (11) and the detector (14) a reflector (19) is located.

10. An electromagnetic hair removal device comprising a light emitting device (1) according to claim 1.

11. Method for emission of light comprising the steps of:
generating at least one operating beam of electromagnetic radiation from an operating beam radiation source,
providing a housing being intransparent for the operating beam having an output opening, wherein the operating beam is generated in the housing, and wherein the operating beam radiation source and the output opening are arranged such that during operation of the device the operating beam is configured to exit the housing through the output opening,
generating at least one sensing beam of electromagnetic radiation from a sensing beam radiation source,
detecting the sensing beam with a detector, after total internal reflection at a contact boundary surface of a sensing window once the contact boundary surface of the sensing window is in contact with air,
wherein the sensing beam radiation source and the at least one detector are located on an identical side of the sensing window, wherein on the side of the sensing window opposing the sensing beam radiation source and the detector a reflector is located wherein the sensing beam is detected by the detector,
wherein the sensing window is positioned in a cross-sectional plane parallel to the contact boundary surface; the contact boundary surface has a saw tooth-like shape and is configured to engage a user's skin during use,
and controlling a controller to produce a generation of the operating beam in a manner that is responsive to the detection of the sensing beam wherein the sensing window is located in the output opening of the housing, wherein the sensing window is made of a material being transparent for the operating beam and for the sensing beam, and wherein during operation the device the operating beam is configured to exit the housing through the sensing window; wherein the operating beam emitted by the operating beam radiation source has a first wavelength, and wherein the sensing beam emitted by the sensing beam radiation source has a second wavelength; and wherein the detector is sensitive only to the second wavelength of the sensing beam.

12. The light emitting device of claim 1, wherein said saw tooth-like shaped sensing window comprises at least two tooth shapes.

13. The light emitting device of claim 1, wherein said saw tooth-like shaped sensing window has a rounded shape.

* * * * *